(12) United States Patent
Alheidt et al.

(10) Patent No.: US 8,512,298 B2
(45) Date of Patent: Aug. 20, 2013

(54) FLUSH SYRINGE HAVING COMPRESSIBLE PLUNGER

(75) Inventors: Thomas A. Alheidt, Stockholm, NJ (US); Tracy Ray Hottovy, Columbus, NE (US); James John Timko, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 707 days.

(21) Appl. No.: 12/117,257

(22) Filed: May 8, 2008

(65) Prior Publication Data

US 2008/0221531 A1    Sep. 11, 2008

Related U.S. Application Data

(63) Continuation of application No. 10/530,831, filed as application No. PCT/US03/29725 on Sep. 23, 2003, now abandoned.

(60) Provisional application No. 60/417,954, filed on Oct. 11, 2002.

(51) Int. Cl.
*A61M 5/315* (2006.01)
(52) U.S. Cl.
USPC .......................................... 604/218; 604/228
(58) Field of Classification Search
USPC ............... 604/187, 218, 222, 225, 228, 229
See application file for complete search history.

(56) References Cited

U.S. PATENT DOCUMENTS

| | | | | | |
|---|---|---|---|---|---|
| 2,886,034 | A | * | 5/1959 | Robinson et al. | 604/222 |
| 2,907,330 | A | * | 10/1959 | Laub | 604/222 |
| 3,147,753 | A | * | 9/1964 | Nogier et al. | 604/222 |
| 3,176,595 | A | * | 4/1965 | Schwartz | 92/243 |
| 3,669,111 | A | * | 6/1972 | Dubner | 604/229 |
| 3,889,673 | A | * | 6/1975 | Dovey et al. | 604/192 |
| 4,064,879 | A | * | 12/1977 | Leibinsohn | 604/121 |
| 4,212,309 | A | * | 7/1980 | Moorehead | 600/579 |
| 4,865,583 | A | * | 9/1989 | Tu | 604/508 |
| 5,735,825 | A | * | 4/1998 | Stevens et al. | 604/218 |
| 5,807,374 | A | | 9/1998 | Caizza et al. | |
| 5,820,601 | A | | 10/1998 | Mayer | |
| 5,899,881 | A | | 5/1999 | Grimard et al. | |
| 6,004,300 | A | * | 12/1999 | Butcher et al. | 604/222 |
| 6,017,330 | A | | 1/2000 | Hitchins et al. | |
| 6,053,894 | A | | 4/2000 | Shadd | |
| 6,361,524 | B1 | * | 3/2002 | Odell et al. | 604/187 |
| 7,087,037 | B2 | * | 8/2006 | Chiba et al. | 604/38 |

* cited by examiner

*Primary Examiner* — Kevin C Sirmons
*Assistant Examiner* — Andrew Gilbert
(74) *Attorney, Agent, or Firm* — Servilla Whitney LLC

(57) ABSTRACT

An I.V. flush syringe assembly includes a barrel having an inside surface defining a chamber for retaining fluid, an open proximal end and a distal end with a passageway therethrough in fluid communication with the chamber. An elongate plunger having a proximal end, a distal end and a stopper is slidably positioned in fluid-tight engagement with the inside surface of the barrel for drawing fluid into and out of the chamber by movement of the stopper relative to the barrel. The plunger includes anti-reflux structure for minimizing stopper deflection when fluid has been delivered from the chamber and the stopper is being forced against the distal end of the chamber.

9 Claims, 9 Drawing Sheets

FLUSH SYRINGE HAVING COMPRESSIBLE PLUNGER

This application is a continuation of U.S. application Ser. No. 10/530,831 filed Apr. 8, 2005, now abandoned, which is a 371 off Application No. PCT/US03/29725 filed Sep. 23, 2003 which claims priority from U.S. Provisional Application No. 60/417,954, filed Oct. 11, 2002.

BACKGROUND OF THE INVENTION

The present invention relates to syringe assemblies and particularly to syringe assemblies for use in I.V. flush procedures.

An I.V. catheter is a commonly used therapeutic device. Many patients, in accordance with their therapy, have an I.V. catheter connected to a vein ready for use in various procedures or in fluid communication with an I.V. system for infusing liquids and medication. Many I.V. sets have I.V. ports which are in fluid communication with a catheter and allow access for the purpose of injecting medication into the patient, and for use in flushing techniques to maintain catheter integrity. Healthcare facilities have flushing protocols which depend on the amount of time the catheter will remain in the patient and the type of catheter being used. For example, a peripherally inserted central catheter (PICC) is a long flexible catheter, which is typically inserted into the central venous system (optimally with the tip terminating in the superior vena cava) via the superficial veins of the antecubital fossa. PICC lines are designed for use when intermediate or long-term therapy is prescribed.

These catheter lines must be periodically flushed with saline flush solution and/or heparin lock flush solution depending on the protocol. Among other things, flushing saline solution removes blood from the catheter and heparin helps prevent the formation of future blood clots. The most common I.V. ports are covered by pierceable septums or pre-slit septums and are known in the art and sometimes referred to as "PRN" from the Latin pro re nata meaning "as the need arises". The septum is preferably made of rubber or another elastomeric material which permits insertion of a sharp needle cannula in order to infuse fluids into or to withdraw fluids from the catheter. Upon withdrawal of the needle cannula the septum seals itself. Ports having pre-slit septums are used with blunt cannula. Typically, the blunt cannula is attached to a syringe and the syringe is moved to place a gentle pressure on the pre-slit septum which is forced open by the blunt cannula to establish fluid communication. Also, some I.V. sets have access valves which are responsive to the frusto-conically shaped tip of a syringe barrel for allowing fluid communication between the interior of the syringe and the catheter without the use of a cannula.

Catheters are flushed using syringe assemblies filled with various fluids. In some cases, different fluids are injected sequentially in accordance with the protocol. For example, a saline solution followed by an anticoagulant such as heparin. The size of the syringe used to flush I.V. lines varies by various factors including the size and length of the catheter. Typically syringes of 1 ml, 3 ml, 5 ml and 10 ml volume are used.

It is important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve slowly withdrawing the syringe and cannula from the I.V. port while still applying pressure to the syringe plunger rod during the flush procedure. When using a syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size drawing liquid from the catheter into the syringe barrel. This is undesirable, since it can cause blood to enter the catheter at the catheter distal end (reflux).

Therefore there is a need for simple, straight forward easy-to-manufacture syringe assemblies which helps reduce or eliminate reflux of blood into the catheter during and after the flushing procedure has occurred without changing flush protocols and procedures.

SUMMARY OF THE INVENTION

The present invention is directed to a syringe for use in flush applications. The syringe reduces or eliminates compression of distal end of the stopper at the completion of the flush procedure thereby reducing or eliminating reflux of blood into the catheter. Compression of the stopper is eliminated, or greatly reduced, by the presence of a compressible or flexible portion disposed on the plunger to absorb the compression forces usually absorbed by the stopper. Since compression of the stopper is translated to a portion of the plunger, reflux is reduced or eliminated.

An I.V. flush syringe assembly includes a barrel having an inside surface defining a chamber for retaining fluid, an open proximal end and a distal end including a distal wall with an elongate tip extending distally therefrom having a passageway therethrough in fluid communication with the chamber. A plunger including an elongate body portion having a proximal end, a distal end and a stopper is slidably positioned in fluid-tight engagement with the inside surface of barrel for drawing fluid into and driving fluid out of the chamber by movement of the stopper relative to the barrel. The elongate body portion of the plunger extends outwardly from the open proximal end of the barrel. The I.V. flush syringe includes anti-reflux means for minimizing stopper deflection when fluid has been delivered from the chamber and the stopper is in contact with the distal wall. Such anti-reflux means provides a portion of the stopper and/or plunger which is more flexible than the distal end of the stopper so that distally directed forces on the plunger will not cause distortion of the distal end of the stopper because anti-reflux structure between the distal end of the stopper and the proximal end of the plunger rod deflects in response to the force.

The anti-reflux structure can include the stopper being supported by a flexible base at the distal end of the plunger wherein the base is more flexible than the stopper in response to proximally directed forces on the stopper.

The anti-reflux structure may include a stopper having a recess in its proximal end and a flexible base extending distally from the plunger wherein the base is positioned at least partially in the recess of the stopper and the base is softer than the stopper and deflectable upon application of a proximally directed force on the stopper.

The anti-reflux structure may include the stopper being connected to a base at the distal end of the plunger wherein the stopper is configured to be more flexible at its proximal end than at its distal end in response to proximally directed forces on the stopper.

The anti-reflux means may include a resilient portion in the plunger between the proximal end and the distal end of the plunger wherein the resilient portion is more deflectable than the stopper and deflectable upon application of a proximally directed force on the stopper.

A method of flushing a catheter of the present invention comprises the steps of providing a syringe assembly having an inside surface defining a chamber for retaining fluid, an open proximal end and a distal end including a distal wall with an elongate tip extending distally therefrom having a passageway therethrough in fluid communication with the chamber, a plunger including an elongate body portion having a proximal end, a distal end and a stopper slidably positioned in fluid-tight engagement with the inside surface of the barrel for drawing fluid into and driving fluid out of the chamber by movement of the stopper relative to the barrel, the elongate body portion extending outwardly from the open proximal end of the barrel, a quantity of flush solution in said chamber, and anti-reflux means for minimizing stopper deflection when the flush solution has been delivered from the chamber and the stopper is in contact with and pressed against the distal wall. The method further includes providing a catheter having a proximal end, a distal end and a passageway therethrough and a housing having a hollow interior in fluid communication with the passageway, the housing having an access valve capable of engaging the elongate tip of the barrel for allowing fluid communication with the hollow interior of the housing. The method further includes the steps of placing the distal end of the catheter in a blood vessel; engaging the elongate tip of the barrel with the access valve so that the passageway in the tip is in fluid communication with the hollow interior of the housing; applying force to the plunger to move the plunger in a distal direction with respect to the barrel so that the flush solution in the chamber flows through the passageway into the hollow chamber of the housing and through the passageway of the catheter; continuing to apply force to the plunger until the stopper contacts and presses against the distal wall of the barrel; and disengaging the barrel from the access valve.

An alternative method may include the step of attaching a needle assembly to the elongate tip of the barrel. The needle assembly includes a cannula having a proximal end, a distal end and a lumen therethrough and a hub having an open proximal end containing a cavity and a distal end attached to the proximal end of the cannula so that the lumen is in fluid communication with the cavity. The attachment of the needle assembly to the barrel is through frictional engagement between the cavity in the hub and the elongate tip. This alternative method is used with a catheter having a proximal end, a distal end and a passageway therethrough and a housing having a hollow interior connected to the catheter and in fluid communication with the passageway of the catheter. The housing further includes a septum for allowing fluid communication with the hollow interior. Fluid communication is established by forcing the distal end of the cannula through the septum so that the lumen of the cannula is in fluid communication with the hollow interior of the housing. Also, the cannula may be permanently attached to the barrel tip with or without the use of a hub.

DETAILED DESCRIPTION

Figure 1:
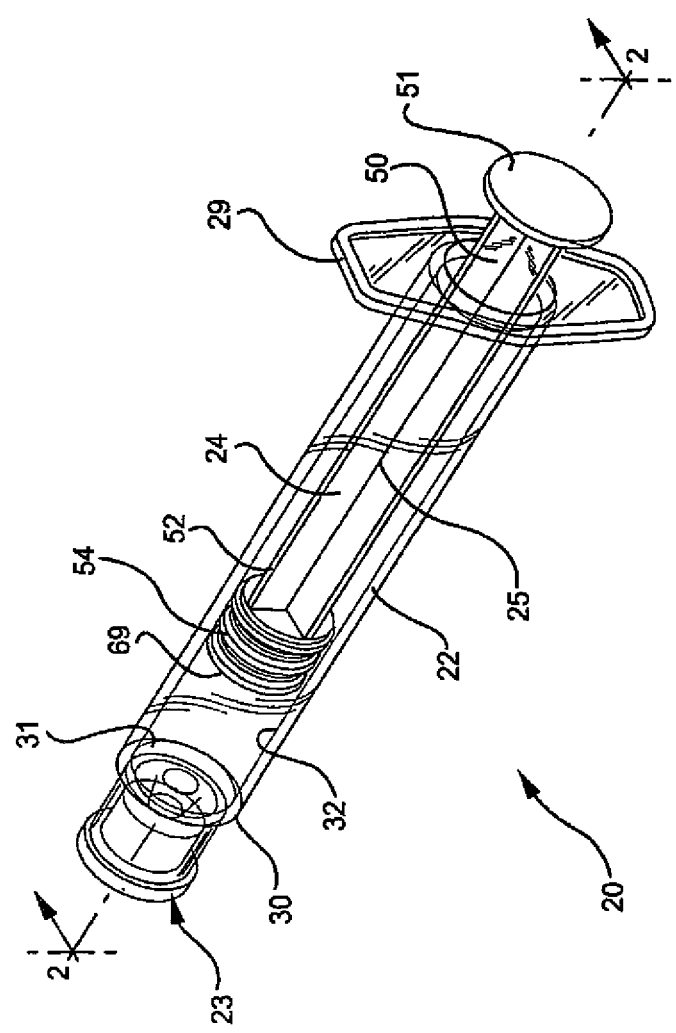
FIG. 1 is a perspective view of a syringe assembly according to one embodiment of the invention.
Figure 2:
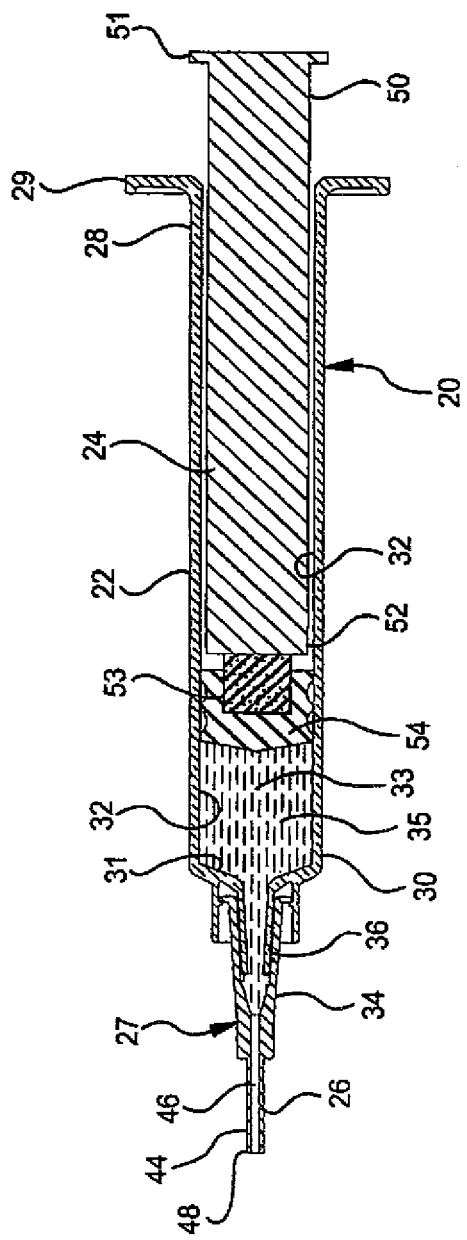
FIG. 2 is a partially cross-sectioned perspective view of the syringe assembly of FIG. 1 with a needle assembly attached.
Figure 3:
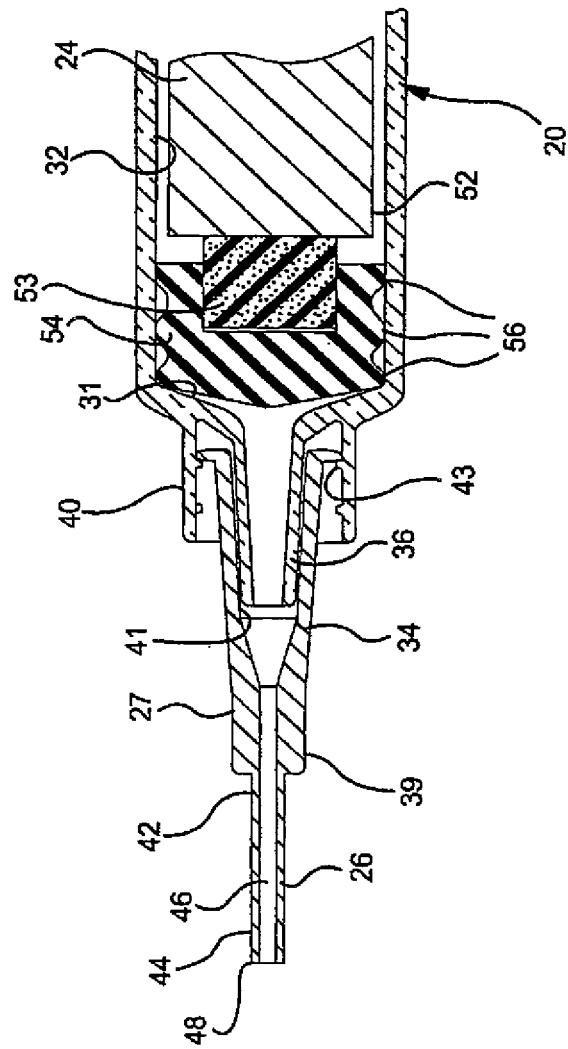
FIG. 3 is an enlarged partial cross-sectional side elevation view of the distal end of the syringe assembly of FIG. 2.

FIG. 1 shows a syringe 20 according to the present invention generally comprising a barrel 22 and a plunger 24. The barrel 22 has a generally elongate body including an open proximal end 28 having finger grips 29, a distal end 30 having a distal wall 31 and an inside surface 32 defining a chamber 33 for retaining fluid. The distal end 30 further includes a tip 36 having a passageway 38 in fluid communication with the chamber. The distal end of barrel 22 preferably, but not necessarily includes a locking luer type collar 40 concentrically surrounding tip 36. The inside surface of the collar includes at least one thread 43. A cannula 26 includes a proximal end 42, a distal end 44 and a lumen 46 therethrough. The distal end may include a sharp tip or a blunt tip 48 as shown. The cannula may be connected directly to the tip of the syringe barrel to establish fluid communication between the lumen and the chamber. Also, the cannula may be part of a needle assembly 27 including a hub 34 having an open proximal end 37 containing a cavity 41 and a distal end 39 attached to the proximal end of the cannula so that the lumen of the cannula is in fluid communication with the cavity. The cavity of the hub can be removably frictionally engaged to the tip of the barrel as illustrated in FIGS. 2-3.

Plunger 24 includes an elongate body portion 25, a proximal end 50 having a flange 51, and a distal end 52. A flexible base 53 extends axially from distal end 52 of the plunger 24. Base 53 has a diameter smaller than the diameter of the plunger 24 and may include threads.

A stopper 54 is disposed on flexible base 53 at distal end 52 of the plunger, preferably via threading engagement. Thus, the flexible base 53 supports the stopper 54 at its center. Stopper 54 includes a plurality of ribs 56 on its outside diameter. The stopper 53 may be made of any material suitable for providing sealing characteristics while under compression. For example, the stopper may be made of thermoplastic elastomers, natural rubber, synthetic rubber, silicon or thermoplastic materials. The base in this embodiment is preferably made of material which is more flexible than the stopper such as thermoplastic elastomers, natural rubber, synthetic rubber, polyurethane, silicone and the like.

In operation, syringe 20 is connected to a hypodermic needle assembly and filled with flush solution using known methods. The flush solution may be any solution intended for flushing. It is preferred that the flush solution be selected from the group consisting of saline flush solution and heparin lock flush solution. These solutions are known in the art and readily available. An example of a saline flush solution is 0.9% Sodium Chloride USP. An example of a heparin lock flush solution is 0.9% Sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial containing flush solution and the flush solution is drawn into the syringe barrel by pulling plunger rod flange 51 in the proximal direction while holding barrel 22, to draw fluid through the needle cannula into the fluid chamber 34.

Alternatively, the syringe may be filled with flush solution during the manufacturing of the syringe via a sterile filling method. Such prefilled syringes may be supplied with a tip cap such as tip cap 23 releasably connected to tip 36 sealing passageway 38. It is preferred that the tip cap is formed of material selected from the group of thermoplastic materials and elastomeric materials such as natural and synthetic rubber and thermoplastic elastomers.

Figure 4:
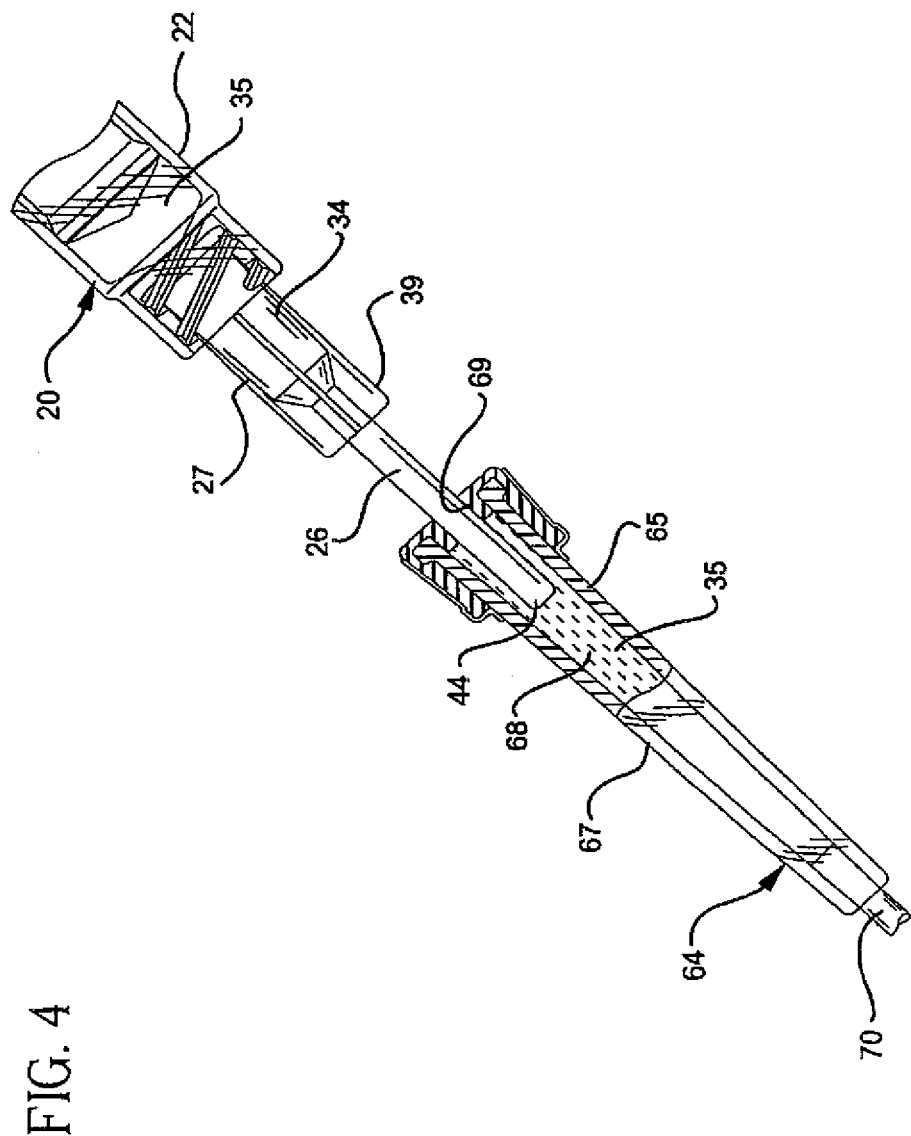
FIG. 4 is a side-elevational view illustrating the syringe assembly in use with a catheter injection site.

The syringe is now ready for use in flushing a catheter of an I.V. set. I.V. sets can be very complicated and may include multiple injection ports, a valve and/or other components. For the purpose of illustrating the present invention a simplified I.V. set 64 is illustrated in FIG. 4. I.V. set 64 comprises an I.V. site 65 which includes a housing 67 having a hollow interior 68 and a septum 69 at its proximal end. A catheter 70 having a conduit therethrough extends from the distal end of the housing. For this I.V. set septum 69 is pre-slit for use with blunt cannula. The I.V. site may be a valve having structure for accepting the syringe barrel tip and being activated by the insertion of the tip to establish fluid communication with the catheter, such as the valve taught in U.S. Pat. No. 6,171,287.

Blunt tip 48 of cannula 26 may be inserted through pre-split septum 69 of I.V. set 64. Alternatively, a sharp tip of a needle cannula may be used to pierce a septum that is not pre-slit or the tip of the barrel may be engaged with a valve in the IV site. This establishes fluid communication between the interior 68 of the I.V. set and the chamber of the syringe barrel. The syringe barrel 22 is preferably held via finger grips 29. Pressure is then applied to flange 51 of the plunger, for example by a thumb, in the distal direction. This moves the plunger 24 having the stopper 54 on its distal end forcing the liquid such as flush solution 35 in the chamber 34 out of the chamber, through cannula 26 and into interior 68 of the I.V. set and then through catheter 70.

Referring to FIG. 3 the position of the plunger and stopper at the completion of the flush procedure is shown. As shown, the flange 51 does not contact the proximal end of the barrel at the completion of the flush procedure. It is preferable, however, that the flange 51 of the plunger bottoms out on the proximal end of the plunger at the completion of the flush procedure. When the distal face of the stopper 54 contacts the distal end 30 of the barrel 22, compressive force generated by this contact is translated to the flexible base 53. Thus, compression of the stopper 54 and its ribs 56 is reduced. The flexible base 53, therefore, absorbs compressive forces so that compression of the stopper face and the outside diameter of the stopper is reduced. Since the stopper 54 does not compress substantially, there is little or no reflux of liquid into the catheter that typically results from the expansion of the stopper after compression.

Figure 5:
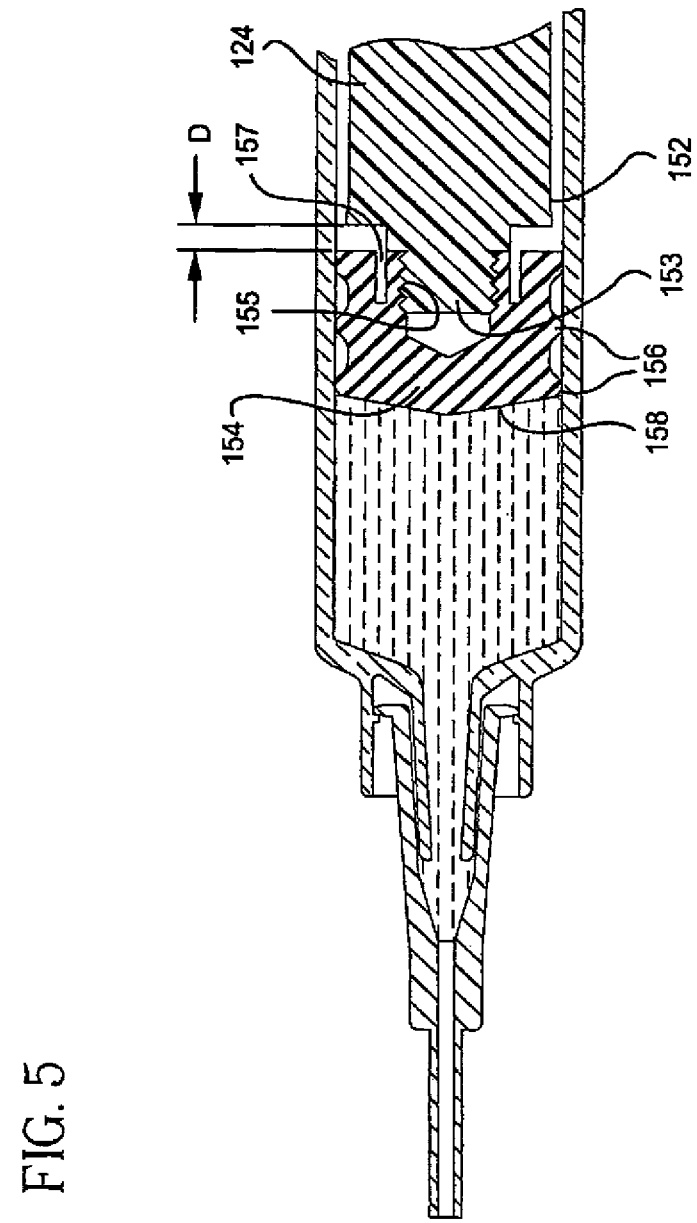
FIG. 5 is a cross sectional side elevation view of the distal end of a plunger and stopper according to another embodiment of the invention
Figure 6:
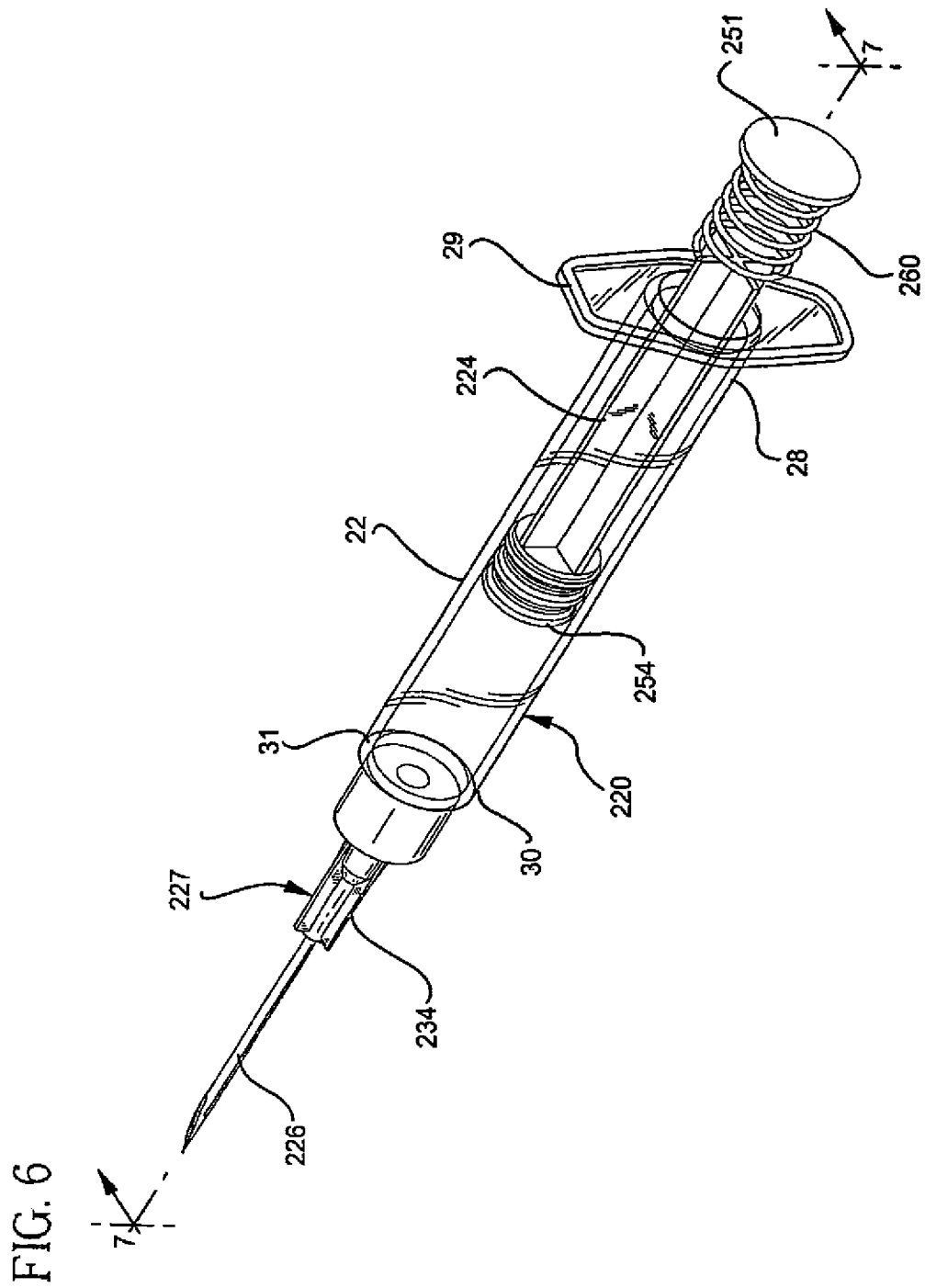
FIG. 6 is a perspective view of a syringe assembly according to another embodiment of the invention.
Figure 7:
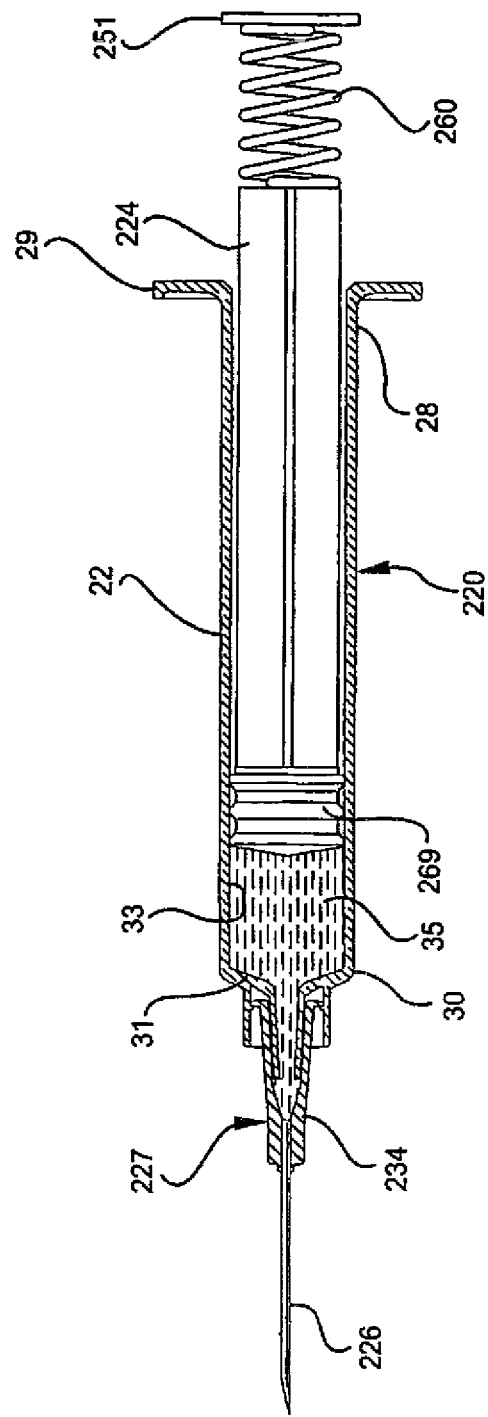
FIG. 7 is partially cross-sectioned side-elevation view of the syringe assembly of FIG. 6.
Figure 8:
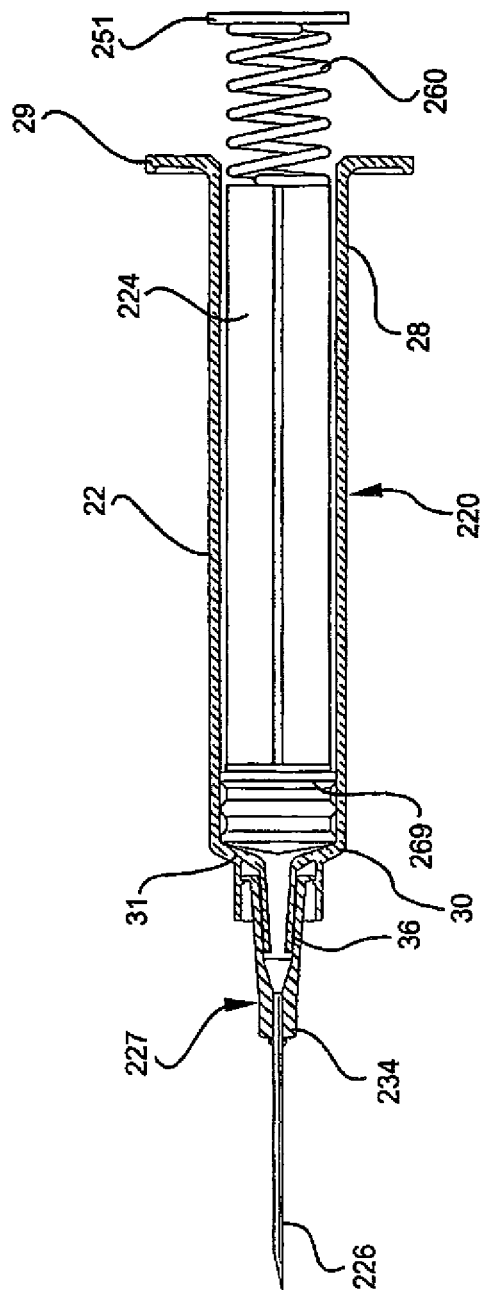
FIG. 8 is the syringe assembly of FIG. 7 shown after flush solution has been delivered.
Figure 9:
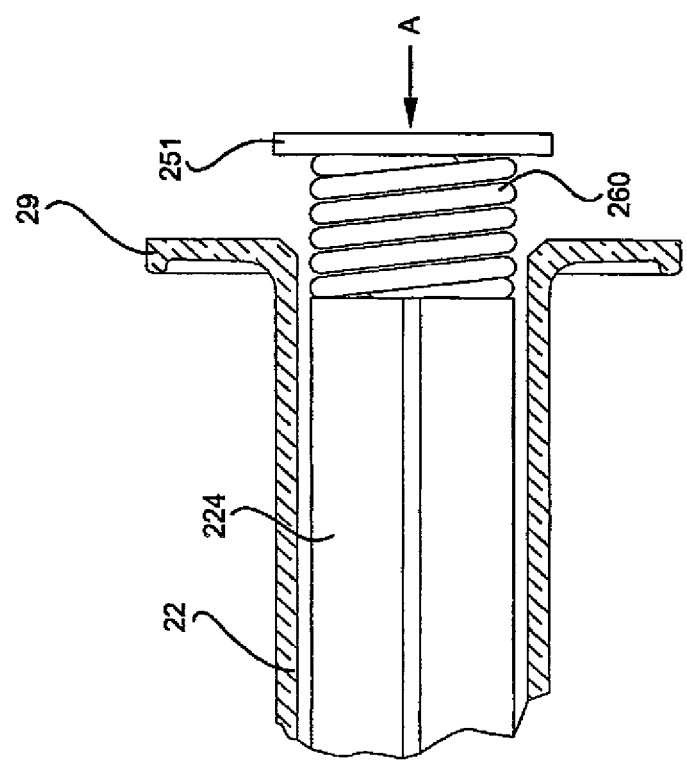
FIG. 9 is a partial cross-sectional view of the proximal end of the syringe assembly of FIG. 8 with the plunger deflected.

FIG. 5 shows another embodiment of the invention. A distal end 152 of a plunger 124 is shown having a base 153 extending therefrom. A stopper 154 is disposed on the base. Base 153 includes threads 155 for threading engagement with the interior of the stopper. Stopper 154 includes one or more ribs 156 on its outer diameter. The stopper further includes an annular groove 157 concentrically surrounding base 153. As shown, the proximal end of the stopper 154 is displaced from the proximal end of the base by a distance denoted as D.

In operation, the flush procedure is carried out as described above. At the completion of the flush procedure, stopper 154 contacts the distal end of the barrel. When distal face 158 of the stopper contacts the distal wall of barrel, compressive force generated by this contact is translated to the proximal end of the stopper in the area of the annular groove which is, by virtue of its structure more flexible than the distal end of the stopper. The annular groove 157 and relief D act to create a structure wherein the proximal end of the stopper as it is connected to the base, is more flexible than the distal end of the stopper to absorb much of the compressive force. Thus, the distal end of stopper 154 and its ribs 156 are subject to less compression. The flexible proximal end of the stopper absorbs most of the compression forces so that the outside diameter near the face of the stopper does not compress. Since the distal end of stopper 154 does not compress as much as a more rigid stopper design, there is little or no reflux of liquid into the barrel 22.

FIGS. 6-9 show another embodiment of the present invention, where like elements are similarly numbered. In this embodiment of the invention, the plunger 224 comprises a flexible or compressible portion 260 at its proximal end 250. The compressible portion 260 may be, for example a compressible spring such as a coil spring or flexible members. As shown, the compressible portion 260 comprises a compressible spring including a plurality of ribs 262.

In operation, after the syringe barrel has been filled with flush solution as discussed above, the sharp tip 248 of the cannula 226 may be inserted through a septum of an I.V. set. Alternatively, a blunt tip of a needle cannula may be used to pierce a pre-slit septum. This establishes fluid communication between the catheter of the I.V. set and the chamber 33 of the syringe barrel. The syringe barrel 22 is preferably held via finger grips 29. Pressure is then applied to the flange 251 of the plunger, for example by a thumb, in the distal direction. This moves the plunger 224 having the stopper 254 on its distal end forcing the liquid in the chamber 33 out of the chamber, through the cannula 226 and into the conduit of the I.V. set through the catheter.

At the completion of the flush procedure, the distal end of the stopper contacts and presses against the distal wall of the barrel. The compressible portion 260 absorbs more of the compressive forces generated by this stopper contact rather than the stopper 254. In addition, if stopper 254 does in fact compress, any relaxation that is caused by the compression of stopper 254 can be translated to and absorbed by the compressible portion 160.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. An I.V. flush syringe assembly comprising: a barrel having an inside surface defining a chamber for retaining flush fluid, an open proximal end and a distal end including a distal wall with an elongate tip extending distally therefrom having a passageway therethrough in fluid communication with said chamber; and a plunger including an elongate body portion having a proximal end, a distal end including a flexible base extending axially therefrom, and a stopper made from a material and supported by said flexible base and being slidably positioned in fluid-tight engagement with said inside surface of said barrel for drawing fluid into and driving fluid out of said chamber by movement of said stopper relative to said barrel, said elongate body portion extending outwardly from said open proximal end of said barrel and said flexible base being made of a material more flexible than said stopper material in response to proximally directed forces; wherein deflection of said stopper is minimized when fluid has been delivered from said chamber and said stopper is in contact with said distal wall.

2. The syringe assembly of claim 1 wherein said stopper defines a recess in its proximal end and said flexible base is positioned at least partially in said recess.

3. The syringe assembly of claim 1 including flush solution in said chamber.

4. The syringe assembly of claim 1 further including a tip cap releasably connected to said tip of said syringe barrel for sealing said passageway.

5. The syringe assembly of claim 4 wherein said flush solution is selected from the group consisting of saline flush solution and heparin lock flush solution.

6. The syringe assembly of claim 1 wherein said flexible base is made of material selected from the list consisting of natural rubber, synthetic rubber, thermoplastic elastomers and combinations thereof.

7. The syringe assembly of claim 1 further comprising a needle assembly including a cannula having a proximal end, a distal end and a lumen therethrough, and a hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

8. The syringe assembly of claim 1, wherein said base includes threads for engaging said stopper.

9. The syringe assembly of claim 1, wherein the base does not include a spring.

* * * * *